United States Patent
Ozer et al.

(10) Patent No.: US 9,517,215 B2
(45) Date of Patent: Dec. 13, 2016

(54) DERMAL MATRIX AND PRODUCTION METHOD THEREOF HAVING SYNERGISTIC EFFECTS COMPRISING MICROPARTICLES WHICH PROVIDES TISSUE REPAIR

(71) Applicant: T.C. EGE UNIVERSITESI, Izmir (TR)

(72) Inventors: Kevser Ozgen Ozer, Izmir (TR); Evren Homan Gokce, Izmir (TR); Ipek Eroglu, Izmir (TR); Sakine Tuncay Tanriverdi, Izmir (TR)

(73) Assignee: T.C. EGE UNIVERSITESI, Izmir (TR)

( * ) Notice: Subject to any disclaimer, the term of this patent is extended or adjusted under 35 U.S.C. 154(b) by 0 days.

(21) Appl. No.: 14/907,563

(22) PCT Filed: Jul. 7, 2014

(86) PCT No.: PCT/TR2014/000251
§ 371 (c)(1),
(2) Date: Jan. 25, 2016

(87) PCT Pub. No.: WO2015/012775
PCT Pub. Date: Jan. 29, 2015

(65) Prior Publication Data
US 2016/0151302 A1 Jun. 2, 2016

(30) Foreign Application Priority Data

Jul. 25, 2013 (TR) .............................. a 2013 09048

(51) Int. Cl.
| | |
|---|---|
| A61L 27/24 | (2006.01) |
| A61L 27/26 | (2006.01) |
| A61L 27/54 | (2006.01) |
| A61L 27/60 | (2006.01) |
| A61L 27/56 | (2006.01) |

(Continued)

(52) U.S. Cl.
CPC ................ *A61K 31/05* (2013.01); *A61L 27/24* (2013.01); *A61L 27/26* (2013.01); *A61L 27/54* (2013.01); *A61L 27/56* (2013.01); *A61L 27/60* (2013.01); *A61L 2300/428* (2013.01); *A61L 2300/622* (2013.01)

(58) Field of Classification Search
CPC .......... A61L 27/56; A61L 27/26; A61L 27/54; A61L 89/06; A61L 89/00; A61L 2300/622; A61L 2300/428; A61L 27/24; A61L 27/60; C08L 89/06; C08L 89/00; A61K 31/05
USPC ....................................................... 514/733
See application file for complete search history.

(56) References Cited

FOREIGN PATENT DOCUMENTS

KR  20000013701 A  3/2000

OTHER PUBLICATIONS

Eroglu et al. ("Evaluation of characteristics and in vitro antioxidant properties of RSV loaded hyaluronic acid—DPPC microparticles as a wound healing system" in Colloids and Surfaces: Biointerfaces, vol. 126, 50-57, 2015.)*

(Continued)

*Primary Examiner* — Blessing M Fubara
(74) *Attorney, Agent, or Firm* — Gokalp Bayramoglu

(57) ABSTRACT

This invention is related to dermal matrices and production method thereof, having within its structure micro particles having antioxidant agents with synergistic effects, providing speedy repair of the dermal tissue, used in chronic wound treatments, basically comprising the steps of preparing the dermal matrix system (11), forming micro particles (12), combining the micro particles with the dermal matrix system.

9 Claims, 1 Drawing Sheet

(51) Int. Cl.
*C08L 89/00* (2006.01)
*A61K 31/05* (2006.01)

(56) References Cited

OTHER PUBLICATIONS

CN 101632841 B, 2012 Google Translated.*
Jong Eun Lee et al: "An Infection-Preventing Bilayered Collagen Membrane Containing Antibiotic-Loaded Hayluronan Microparticles: Phyiscal and Biological Properties", Artificial Organs, Jan. 1, 2002, pp. 636-646, XP055032851,Retrieved from the Internet: URL:http://onlinelibrary. wiley.com/store/10.1046/j.1525-1594.2002.06847.x/asset/j.1525-1594.2002.06847.x.pdf?v=1 &t=h4pj99jp&s=f5a488e25f9c220b81d3821b166170da3336209.
International Journal of Nanomediceine, Apr. 1, 2012, p. 1841, XP055155456, DOI: 10.2147/IJN. S29710.

* cited by examiner

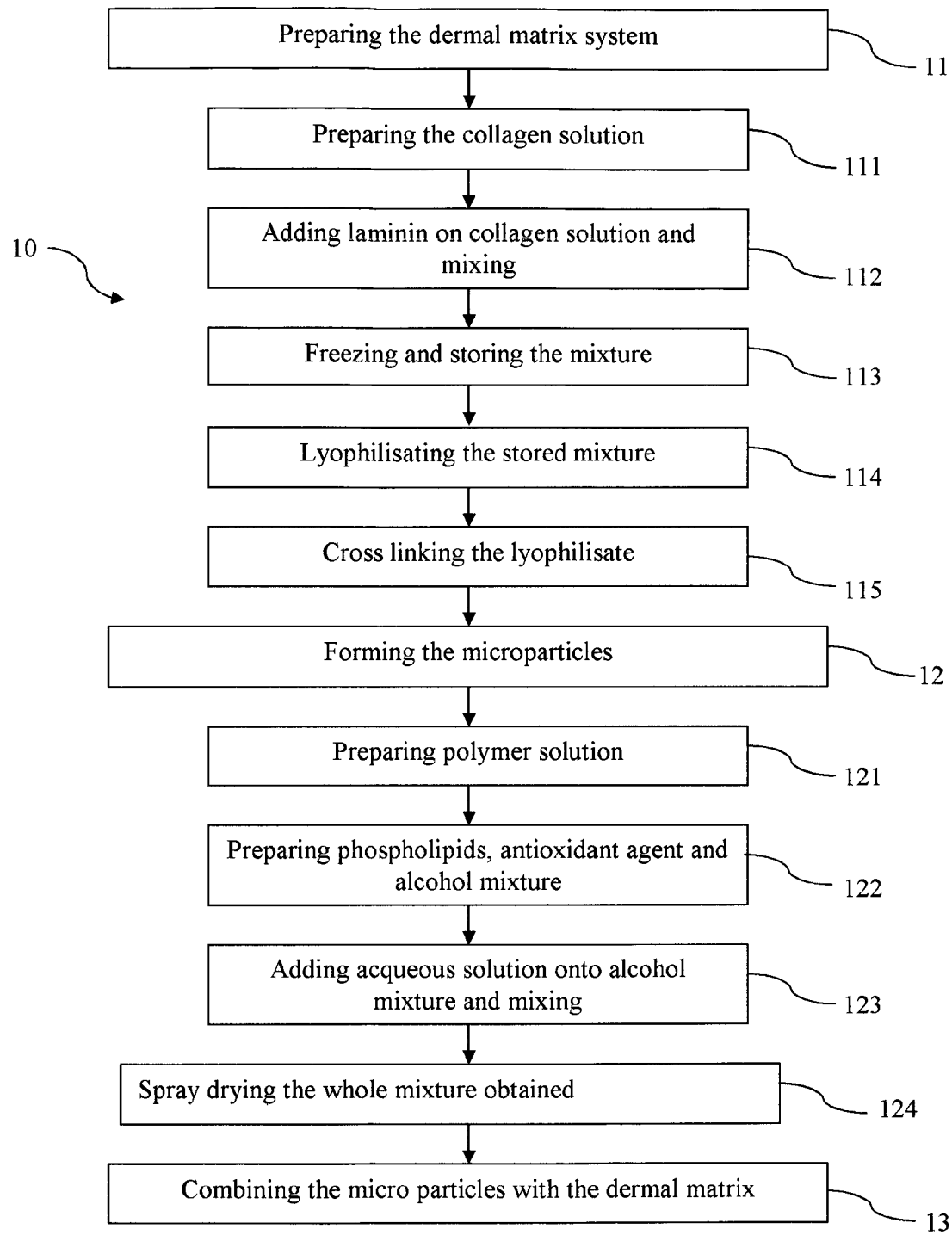

DERMAL MATRIX AND PRODUCTION METHOD THEREOF HAVING SYNERGISTIC EFFECTS COMPRISING MICROPARTICLES WHICH PROVIDES TISSUE REPAIR

TECHNICAL FIELD

This invention is related to dermal matrices and production method thereof used in treating chronic wounds, which enables the speedy repair of the dermal tissue, and which comprises within its structure micro particles having antioxidant agents with synergistic effects.

BACKGROUND

Conventional products such as crimes, gels, lotions and ointments are used in treating chronic wounds nowadays. In order for said products to be effective in treatment, they need to be applied frequently. Moreover, the application dose must also be standardized.

There are however current treatments that could eliminate these problems which are a part of the conventional approach. In such treatment applications xenograft and graft transfer methods are used in order to replace new tissues over areas with large tissue losses. These methods are both painful and at the same time could have donor based disadvantages.

The most up to date final stage known in chronic wound treatments, comprise innovative formulations. Micro particle systems and matrix systems provide advantageous treatment methods when compared with the prior art methods. As a result of the literature research carried out, it has been observed that matrices comprising agents that help heal the area, and which provide the necessary mechanical support, compensating via and occlusive effect the lost tissue area as a result of various injuries, has been developed. Dermal matrices have been prepared especially comprising collagen-chitosan, collagen-gelatin, collagen-glycosaminoglycans, and collagen-hyaluronic acid compositions and by incubating fibroblast to these and healing of the wound tissue has been observed.

Dermal matrices are systems prepared with natural or synthetic polymers in order to effectively support cell growth and development and the usage of these in treating wounds have opened up a new horizon. The main aim of these structures is to re-develop the tissue that has been damaged and to carry different biomaterials and bioactive molecules to this region.

Nowadays commercial products that heal the epithelium having different characteristics are present. In said products wound patches prepared with chitosan which is a natural polymer is used, or polymers such as synthetic polyurethanes and PLGA are used and a medium where keratinocytes form small colonies in the epidermis is provided, and thereby a faster epithelium formation is obtained. In said products where epithelium is replaced, a two dimensional structure is provided. This dimension preferred in the formation of epithelium however is not sufficient in substituent treatments that require three dimensional structures.

The wound area is open to infection and similar complications and the most effective approach in preventing the infections are to provide effective treatment as soon as possible. The first six hours is the more important time span in terms of bacterial colonization formation after getting wounded. The most effective method in preventing infections are to seal off the wound by using sterile patches over the wounds and cleaning the wound under aseptic conditions before sealing it with a sterile patch, these conditions are even more effective than antibiotic treatment. For this reason, immediately covering the wound, increasing the self repair of the dermal layer, and developing fully layered tissues that shall replace the tissue area are some of the crucial subjects that need to be addressed in the current studies.

Conventional approaches (ointments, crimes, gels, lotions) used in treating wounds, are not capable of overcoming basic problems such as infections of wounds, dehydration, heat loss, for live tissue to remain unprotected, protein, erythrocyte, leukocyte, immune agents and oligoelement losses.

One of the most important disadvantages of conventional formulations, is that the amount applied may change or vary and as a result the applied dose cannot be standardized and the application needs to be carried out frequently. Every time the application is carried out, the patient feels pain and this makes the treatment procedure more difficult. Moreover, allergic reactions could arise due to the surface active agent, or components such as preservatives and perfume used in these formulations. Besides conventional therapy, graft transfer, which is another treatment carried out in case of large tissue loss cases also has many disadvantages. These disadvantages can be diseases that are transmitted from the donor, or formation of new wounds at the donor area from which the graft was taken from. Although autografts are materials that are preferred, in some cases there may not be any suitable skin tissue that can be transferred in patients. In addition to this, a new wound is present at the area where the graft tissue is taken from. Another disadvantage is that these procedures may necessitate surgical operations. Innovative approaches were deemed necessary to shorten the treatment time, in order to prevent complications such as infections and in order to overcome said disadvantages.

The formulations that have been prepared in order to reach these aims, having collagen, chitosan and gelatin, are two dimensional systems, and said two dimensional systems were not sufficient enough to provide physical support. In order to overcome this problem, and the methods used to ensure that the dermal matrices prepared using collagen were three dimensional comprising chemical materials, ruin the conditions that need to be present for cell growth. In the present technique, the products developed to reach said aims do not comprise micro particles and they act like a wound patch wherein cells can grow a little bit faster.

SUMMARY OF THE INVENTION

The aim of the present invention is to provide a dermal matrix, which increases the efficiency of chronic wound treatments and decreases the time of healing and ensures tissue repair.

Another aim of the invention is to provide a dermal matrix not only comprising collagen and laminin but also comprising micro particles which carry antioxidant agents that help to speed up tissue repair speed by showing synergic effects.

Another aim of the invention is to obtain a dermal matrix production method that enables tissue repair, wherein agents formed of proteins located inside the natural structure of the dermis and other components are used.

Another aim of the invention is to provide a dermal matrix production method which supports cell growth and tissue repair, by means of using the cross linking method which is not a chemical method.

Another aim of the invention is to provide a dermal matrix production method which enables tissue repair and prevents heat sensitive bio materials from degrading by applying a lyophilisation procedure.

BRIEF DESCRIPTION OF THE DRAWINGS

A dermal matrix production method that provides tissue repair produced in order to reach the aim of this invention has been shown in the attached FIGURE, wherein said FIGURE illustrates the following:

FIG. 1—Is the flow chart of the method subject to the invention.

DETAILED DESCRIPTION OF THE INVENTION

A dermal matrix production method (10) having synergistic effects and providing tissue repair, characterized in that it comprises the steps of:
Preparing the dermal matrix system (11),
preparing the collagen solution system (111),
adding laminin onto collagen solution and mixing (112),
freezing and storing the mixture (113),
Lyophilization of the stored mixture (114),
Cross linking the lyophilisate (115),
Forming micro particles (12),
Preparing aqueous solution of the polymer (121),
Preparing the phospholipid, antioxidant agent and alcohol mixture (122),
adding the aqueous solution onto the alcohol mixture and mixing (123),
spray drying the whole mixture obtained (124),
combining the micro particles with a dermal matrix system (13).

The method (10) subject to the invention is principally based on preparing a dermal matrix system and a micro particle system separately and following this spraying the micro particle onto the dermal matrix thus combining these two systems physically.

According to the method (10) subject to the invention, first of all a collagen solution is prepared (111) by adding collagen to acetic acid solution in order to prepare a dermal matrix system (11). In the preferred application of the invention, collagen is added (111) at a concentration of 0.1% to 0.1 M acetic acid solution.

Following this laminin is added onto the collagen solution (112). In a preferred embodiment of the invention, 2.5 ml of the collagen solution that has been prepared is taken and 20 µl laminin is added, and all of it is mixed in an ice bath (112). When using the ice bath, it is aimed to prevent the deterioration of the protein structures that are present inside the mixture. In a preferred embodiment of the invention, mixing is carried out at a speed of 3000 cycles/minute, for 1 minute, using a 10-G probe.

The mixture comprising collagen and laminin is left to wait for 12 hours at a temperature of −20±1° C. and is frozen (113). Following this, said mixture which has been frozen is subjected to lyophilization for 24 hours (114). Thereby it is ensured that the deterioration of the heat sensitive biomaterials inside said mixture is prevented.

The lyophilisate structure comprising collagen and laminin that has been obtained, is cross linked (115) under 254 nm wavelength using an ultraviolet cross binder (UV-cross linker) device. In another place, an aqueous polymer solution is prepared (121) in order to provide the formation of micro particles (12). In order to ensure this 0.2 g hyaluronic acid sodium salt (HA) is used and it is dissolved in 150 ml pure water. In the meantime, dipalmitoylphosphatidylcholine (DPPC) and resveratrol is mixed into alcohol and is dissolved (122). In a preferred embodiment of the invention, 0.7-0.75 g DPPC and 0.05-0.1 g resveratrol 350 ml is added into ethanol and is mixed (122). Usage of resveratrol (antioxidant) shows synergic effects with collagen and laminin that forms the protein structure, and as a result the efficiency of the end product regarding tissue repair is increased. Besides this, it is ensured that the matrix integrity of the end product is retained for a long time.

The HA solution (121) that has been prepared, is added onto the solution (122) of DPPC and resveratrol in alcohol and is mixed at 40±1° C. (123). The whole mixture that has been prepared is placed inside a spray dryer and micro particles are obtained by spraying (124). In the preferred embodiment of the invention: the spray dryer has been adjusted such that the initial temperature is 180° C., and the spraying speed is 400 L/h.

HA micro particles loaded with resveratrol and prepared with a spray dryer are sprayed onto the previously prepared dermal matrix (11) as dry powder and said two systems are combined (13). According to the preferred embodiment of the invention, the sprayed micro particles comprise 50 µM resveratrol. These matrices that have been obtained, especially are used in chronic wound treatments and they significantly increase the speed of healing of the wound.

In order to determine the diameter and thickness of the dermal matrixes obtained using the method subject to the invention, automatic compass has been used and the diameter and the thicknesses of the matrices have been evaluated. As a result of the analysis that has been carried out, the average diameter of the obtained dermal matrix is 2.24±0.05 cm and their thicknesses have been measured as 0.23±0.04 cm.

It has been determined that the pore sizes of the dermal matrices that have been obtained using scanner electron microscope and confocal microscope in order to determine surface morphology were around at most 100 µm. In addition to this, it has been observed that three dimensional collagen fibers were present and micro particles were cross linked. The matrices that have been prepared for water retention capacity, have been left to wait at 37±1° C. water, for 20 seconds after their weights have been determined. By calculating the percent rate of the initial weight and comparing it to the weight measured after the test is completed, the water retention capacity has been determined to be %84±1.5.

A TA-XT plus texture analysis device has been used in order to determine the mechanical characteristics of dermal matrices. As a result of the analysis, the hardness 26-21 N, compression 23-18 N/mm, cohesion 0.93-1 and elasticity values 0.8-1, have been calculated by way of power, time curves that belong to the matrix. As result of the humidity content determination, the humidity amount of the dermal matrix subject to the invention has been calculated as 0.2%. The sizes of the micro particles located inside the dermal matrix, have been calculated to be between 15-30 µm using the laser diffraction method.

As it can be seen in the images obtained with SEM, the formulations are spherical and have smooth surfaces. The particles sizes observed through SEM, have been compared with the results of the previously carried out laser diffraction distribution method, and the sizes have been found to be consistent.

The drug loading capacity of the micro particles that have been prepared, has been calculated as 0.5-1 mg and the encapsulation efficiency have been calculated to be between %97-%98.7.

In order to determine the release amount of resveratrol from micro particles, active agent release studies have been carried out from micro particle formulations prepared with different resveratrol concentrations. The results of the analysis showed that the released resveratrol amount from the formulations for 24 hours were between %73-85.

The effect of hyaluronidase, collagenase, lipase and phospholipase enzymes in relation to release of resveratrol from micro particles was examined. Separate enzymatic degradation studies have been carried out with hyaluronidase and collagenase enzymes in order to examine the enzyme effect to the dermal matrix. While the dermal matrix which did not comprise micro particles were degraded enzymatically with collagenase in 30 minutes, the degradation of the dermal matrix comprising resveratrol loaded micro particles took twice the amount of time. Resveratrol was not only advantageous in that it supported wound healing but also it was advantageous because it protected the matrix integrity against collagenase for a longer time.

Confocal microscope 3D software program has been used in order to determine if the micro particles were homogenously distributed in the dermal matrix and where they were localized. The confocal study was renewed and the data have been evaluated in this program. The morphological studies carried out showed that the micro particles were distributed much more homogeneously at the top surface of the dermal matrix and that said micro particles were in complete contact with the matrix.

The human dermal fibroblast cells, (Invitrogen C-013-5C) were cultured in humid conditions comprising 37±0.5° C. and 5% $CO_2$ according to the instructions of the producer. Resveratrol solution, has been incubated with formulations that did not comprise resveratrol and micro particle formulations that comprised resveratrol for 24 hours and the effects of all samples regarding cell vitality were examined. As the resveratrol solution, or formulations that are empty or do contain active agents were observed not to have cytotoxic potential and they have shown cell proliferation increasing effects in concentrations that are corresponding to 50 µM resveratrol content. Oxidative stress parameters such as total glutation, malondialdehyde, and superoxide dismutase and glutation peroxidase have been examined inside the cells that have been analyzed. The results that were obtained, were an indication that the dosage type developed for resveratrol comprised oxidative activity at a molecular level.

In conclusion, the studies carried out in the recent years, showed that wound healing were dependent on the components selected inside the formulation and that the innovative formulations comprising proteins that form the natural structure of the dermis provided efficient treatment and treatment time could be shortened. It is obvious that new drug carrying systems need to be prepared for long term wound treatments. There are no new generation formulations that comprise the selected combination. The synergic effect of the dermal matrices with resveratrol in relation to tissue repair has been evaluated for the first time with this invention.

The invention claimed is:

1. A method for producing a dermal matrix system with micro particles, comprising:
   preparing the dermal matrix system;
   preparing the micro particles; and
   combining the micro particles with the dermal matrix system,
   wherein the step of preparing the dermal matrix system further comprises,
      preparing a collagen solution,
      adding laminin into the collagen solution and forming a first mixture,
      freezing and storing the first mixture,
      lyophilizing the first mixture and forming a lyophilizate,
      cross linking the lyophilizate,
   wherein the step of preparing the micro particles further comprises,
      preparing an aqueous polymer solution, wherein the aqueous polymer solution is prepared by dissolving a hyaluronic acid (HA) in pure water,
      preparing a second mixture of phospholipid, an antioxidant agent and alcohol, wherein the second mixture is formed by adding dipalmitoylphosphatidylcholine (DPPC) and resveratrol into the alcohol,
      adding the aqueous polymer solution into the second mixture to form a third mixture,
      drying the third mixture to obtain the micro particles,
   wherein in the step of combining the micro particles with the dermal matrix system, the micro particles are sprayed onto the dermal matrix system.

2. The method for producing a dermal matrix system with micro particles according to claim 1, wherein the dipalmitoylphosphatidylcholine (DPPC) has a weight of 0.7-0.75 g, the resveratrol has a weight of 0.05-0.1 g and the alcohol has a volume of 350 mL.

3. The method for producing a dermal matrix system with micro particles according to claim 1, wherein the step of preparing a second mixture is performed at the temperature of 40±1° C.

4. The method for producing a dermal matrix system with micro particles according to claim 1, wherein in the step of preparing the collagen solution, collagen is added at a concentration of 0.1% into an acetic acid, and the acetic acid has a volume of 0.1M.

5. The method for producing a dermal matrix system with micro particles according to claim 1, wherein in the step of adding the laminin into the collagen solution and forming the first mixture, the collagen solution has a volume of 2.5 mL, the laminin has a volume of 20 µl, and the first mixture is formed in an ice bath.

6. The method for producing a dermal matrix system with micro particles according to claim 1, wherein in the step of freezing and storing the first mixture, the first mixture is left to rest for 12 hours at a temperature of −20±1° C.

7. The method for producing a dermal matrix system with micro particles according to claim 1, wherein the step of lyophilizing the first mixture further comprises lyophilizing the first mixture for 24 hours.

8. The method for producing a dermal matrix system with micro particles according to claim 1, wherein the step of cross linking the lyophilizate further comprises cross linking the lyophilizate under an ultraviolet light with a wavelength of 254 nm, using an ultraviolet cross linker (UV-cross linker) device.

9. The method for producing a dermal matrix system with micro particles according to claim 1, wherein in the step of preparing the aqueous polymer solution, the hyaluronic acid (HA) has a weight of 0.2 g, and the pure water has a volume of 150 mL.

* * * * *